(12) United States Patent
True

(10) Patent No.: US 9,744,531 B2
(45) Date of Patent: Aug. 29, 2017

(54) REGENERATION OF CLAY CATALYSTS FOR ALKYLATION OF AROMATIC RINGS

(71) Applicant: Chemtura Corporation, Middlebury, CT (US)

(72) Inventor: Alan B. True, New Haven, CT (US)

(73) Assignee: LANXESS Solutions US Inc., Middlebury, CT (US)

( * ) Notice: Subject to any disclaimer, the term of this patent is extended or adjusted under 35 U.S.C. 154(b) by 21 days.

(21) Appl. No.: 14/995,250

(22) Filed: Jan. 14, 2016

(65) Prior Publication Data

US 2016/0256864 A1  Sep. 8, 2016

Related U.S. Application Data

(60) Provisional application No. 62/127,688, filed on Mar. 3, 2015.

(51) Int. Cl.
| | |
|---|---|
| *B01J 21/16* | (2006.01) |
| *B01J 21/20* | (2006.01) |
| *B01J 38/50* | (2006.01) |
| *B01J 38/52* | (2006.01) |
| *B01J 38/60* | (2006.01) |
| *B01J 38/62* | (2006.01) |
| *C07C 209/24* | (2006.01) |
| *C07C 209/68* | (2006.01) |
| *B01J 37/06* | (2006.01) |
| *C09K 15/18* | (2006.01) |

(52) U.S. Cl.
CPC ............... *B01J 38/60* (2013.01); *B01J 21/16* (2013.01); *B01J 21/20* (2013.01); *B01J 38/50* (2013.01); *B01J 38/52* (2013.01); *B01J 38/62* (2013.01); *C07C 209/24* (2013.01); *C07C 209/68* (2013.01); *B01J 37/06* (2013.01); *C09K 15/18* (2013.01); *Y02P 20/584* (2015.11)

(58) Field of Classification Search
CPC ... B01J 21/16; B01J 21/20; B01J 38/50; B01J 38/52; B01J 38/60; B01J 38/62; C07C 209/24; C07C 209/68; Y02P 20/584
See application file for complete search history.

(56) References Cited

U.S. PATENT DOCUMENTS

| | | |
|---|---|---|
| 2,102,341 A | 12/1937 | Von Fuchs |
| 2,368,507 A | 1/1945 | Welty, Jr. |
| 3,148,158 A | 9/1964 | Schenck et al. |
| 3,496,230 A | 2/1970 | Kaplan |
| 4,824,601 A | 4/1989 | Franklin |
| 5,672,752 A | 9/1997 | Lai et al. |
| 5,750,787 A | 5/1998 | Lai et al. |
| 5,942,457 A | 8/1999 | Santos |
| 6,204,412 B1 | 3/2001 | Lai |
| 6,315,925 B1 | 11/2001 | Aebli et al. |
| 8,828,916 B2 | 9/2014 | Simard |

FOREIGN PATENT DOCUMENTS

| | | | |
|---|---|---|---|
| AU | 2013258919 A1 | | 11/2014 |
| CA | 2872463 | * | 11/2013 |
| GB | 998186 A | | 7/1965 |
| WO | 2013168608 A1 | | 11/2013 |

OTHER PUBLICATIONS

Chitnis, S.R. et al., "Alkylation of diphenylamine with alpha-methylstyrene and diisobutylene using acid-treated clay catalysts", Journal of Catalysis, vol. 160, pp. 84-94 (1996), Academic Press, Duluth, MN (XP-002085239).
Extended European Search Report dated Jul. 27, 2016 from corresponding EP Application No. 16158189.7, 16 pages.

* cited by examiner

*Primary Examiner* — Paul A Zucker
*Assistant Examiner* — Mark Luderer
(74) *Attorney, Agent, or Firm* — Dilworth IP LLC

(57) ABSTRACT

Catalysts, in particular clay catalysts, use in alkylation reaction of aromatic compounds, e.g., aromatic amines, that have lost activity during use, are regenerated by contacting the used catalyst with a mixture of a minor amount of an acid, in a mixture with water and an organic solvent. The regeneration process is readily incorporated into an alkylation process for aromatic amines.

17 Claims, No Drawings

REGENERATION OF CLAY CATALYSTS FOR ALKYLATION OF AROMATIC RINGS

This application claims benefit under 35 USC 119(e) of U.S. Provisional Application No. 62/127,688, filed Mar. 3, 2015, the disclosure of which is incorporated herein by reference.

Provided is a method for regenerating clay catalysts for use in alkylation reactions of aromatic rings, e.g., aromatic amines, and an alkylation process comprising a step or steps designed for the regeneration of clay catalysts.

BACKGROUND OF THE INVENTION

Alkylated aromatic amines, e.g., diarylamines, such as alkylated diphenylamine, are well known in the art to be effective stabilizers/antioxidants in a wide variety of organic materials, for example, polymeric substances such as natural or synthetic rubber, polyolefins, polystyrenes, condensation polymers, other elastomers and thermoplastics plastics, lubricating oils including e.g., mineral oil derived lubricants and synthetic lubricants, etc. In many these applications, light colored products which are liquid at room temperature are desirable.

A variety of catalysts have been used in the alkylation of aromatic compounds including protic acids, metal based Lewis acids such as aluminum trichloride, and clays. U.S. Pat. No. 3,496,230 discloses the preparation of a mixture of 80% dinonydiphenylamine and 15% nonyldiphenylamine in the presence of Friedel-Crafts catalysts such as $AlCl_3$ and $ZnCl_2$, but mixtures contaminated by traces of chlorine, metal compounds and undesirable by-products, e.g. N-alkylated diphenylamines and diphenylamines alkylated in the 2- and 2'-positions, are obtained, which mixtures are black in color and very viscous.

U.S. Pat. No. 2,943,112 discloses a two-step process whereby alkylation of diphenylamine in the presence of acid catalysts or clay catalysts with relatively unreactive olefins is followed by alkylation with more reactive olefins to scavenge the unreacted diphenylamine. Clay catalysts are reported to provide less color. U.S. Pat. No. 6,204,412 discloses a method of alkylating diphenylamine to obtain a light colored, liquid product, which also comprises a two-step method wherein, in the second step, a second olefin is added to the reaction mixture containing diphenylamine and diisobutylene (and/or an alpha-olefin of the disclosed formula) to scavenge or reduce the amount of unreacted diphenylamine in the product.

Often, mono-alkylation, di-alkylation and poly-alkylation are possible and control over the amount and position of alkylation, e.g., ortho-, para- etc., is required. U.S. Pat. No. 4,824,601 discloses the use of acidic clay catalysts for the alkylation of diphenylamine to produce a light colored, liquid product by reacting certain molar ratios of reactants within specific temperature ranges for a time sufficient to ensure the alkylated product contains less than 25% dialkylated diphenylamine. The limit on the amount of dialkylated diphenylamine is disclosed as necessary to avoid the formation of crystallized, solid products.

U.S. Pat. Nos. 5,672,752 and 5,750,787 disclose processes for alkylating diphenylamine with linear alpha olefins and diisobutylene in the presence of a clay catalyst, which selectively result in a higher proportion of monoalkylated diphenylamine and a lower proportion of unsubstituted diphenylamine and/or disubstituted or polysubstituted diphenylamines.

U.S. Pat. No. 6,315,925 discloses alkylating diphenylamine with an excess of nonene or a mixture of isomeric nonenes in the presence of from 2.0 to 25.0% by weight, based on diphenylamine, of an acidic clay in the absence of a free protonic acid, resulting in a mixture containing at least 68.0% dinonyldiphenylamine, from 20.0 to 30.0% nonyldiphenylamine, not more than 3.5% trinonyldiphenylamine; and not more than 1.0% diphenylamine.

Greater efficiency in the use of starting materials and generation of less waste for disposal is needed; for example, U.S. Pat. No. 8,828,916 discloses a process for preparing nonylated diphenylamines which improves nonenes usage by recycling and reusing stripped unreacted nonenes from an earlier process.

In the catalyzed processes above, the catalyst will become inactivated over time and will be discarded as contaminated waste. This is true for batch processes and continuous processes. A method for regeneration of spent catalyst would allow for the continued use of the catalyst which could reduce costs and waste.

Acidic clays, similar to those useful in alkylation of aromatic compounds, have also been used in industrial processes for removing colored impurities from mineral oils, as catalysts in cracking of hydrocarbons, and other operations. Methods for regenerating clays used in these heavy industry applications are known.

U.S. Pat. No. 2,368,507 discloses a method of regenerating catalysts, such as silica, alumina and acid treated bentonitic clays, useful in cracking, reforming, dehydrogenation or aromatization reactions of hydrocarbon oils, by treating the catalyst with air or hot inert gasses containing regulated quantities of air or oxygen at temperatures high enough to cause combustion of the carbonaceous materials deposited on the catalysts during use.

U.S. Pat. No. 2,102,341 discloses of method of regenerating materials used for decolorizing mineral oils, such as clays, by forming a slurry containing the spent clay in a non-acidic stable solvent in the presence of a volatile basic reacting substance, e.g., ammonia or volatile alkyl amines, which basic reacting substance is absorbed by the clay and thus displacing the absorbed matter on the surface of the spent clay, followed by separating the solvent and displaced matter from the clay and basic reacting substance, and then removing the basic reactive substance from the clay.

U.S. Pat. No. 3,148,158 discloses a process for activating a raw, unused bentonite clay by removing impurities such as certain magnesium, calcium and iron compounds as well as other impurities, the process comprising treating the raw clay with a hydrolyzable inorganic or organic halide, e.g., thionyl chloride, in the presence of a small amount of water and an inert organic diluent, such as an ether, ketone, alcohol, alkane, aromatic hydrocarbon or other organic solvent, at a temperature ranging from ambient to 130° C.

U.S. Pat. No. 5,942,457 discloses a process for regenerating spent clay comprising (1) an extraction stage wherein an organic solvent or mixture of organic solvents are thoroughly mixed with the spent clay thus separating the entrained oil from the spent clay, (2) a reactivation stage wherein the oil-free spent clay is treated with acid, and (3) a thermal polishing step wherein the acid-treated, solvent extracted spent clay is heated at a temperature from 500° F. to 1400° F.

Many of the processes used in regenerating spent clay catalysts for removing colored impurities or in cracking of hydrocarbons etc., employ harsh conditions that may harm a catalyst used in alkylation, especially selective alkylation, of aromatic systems. A process is still needed for regenerating a clay catalyst used in the alkylation of aromatic compounds, e.g., aromatic amines, that is robust enough to remove the material deposited on the clay, e.g., oligomers, amine residues, reactant and product degradation products, etc., but which process does not harm the features of the catalysts that provide the desired reactivity and selectivity during the alkylation reaction.

SUMMARY OF THE INVENTION

Catalysts, e.g., clay catalysts, that have lost activity or selectivity due to use in alkylation reactions are regenerated by a process comprising exposure of the spent catalyst to a regeneration mixture comprising an acid, water, and an organic solvent, often at elevated temperatures.

In the regeneration mixture, the acid, e.g., a mineral acid such as sulfuric acid, phosphoric acid etc., or an organic acid such as acetic acid, is a minor component, generally present in amounts of 20% by weight or less, typically 10% or less, e.g., from 0.1 to 5%. The amount of water will vary depending in part of the organic solvent being used, but typically less than 45% of the regeneration mixture is water, often 25% or less. The organic solvent makes up at least 35% by weight of the regeneration mixture, typically the solvent is present in amounts of 40% or more and is often the majority component of the regeneration mixture, i.e., present in amounts of greater than 50% by weight. The organic solvent is not particularly limited and more than one solvent may be present.

The spent catalyst may be soaked in the regeneration mixture for up to 36 hours, or the regeneration mixture may be passed through the spent catalyst, which may also take several hours. After exposure to the regeneration mixture, the catalyst is separated from the regeneration mixture and may be further treated, for example, to remove residual traces of the regeneration mixture, or to recondition the catalyst to remove water that may still be present.

The catalysts, and the process for regenerating them, are useful in alkylation reactions. In many embodiments of the invention the regeneration process is part of a process for alkylating aromatic amines. For example, in one particular embodiment, the catalyst regeneration process is part of process for alkylating diarylamines such as diphenylamine, dinaphthylamine, N-phenyl-N-naphthyl amine etc., with olefins, e.g., nonenes, isobutylene, oligomers of isobutylene, oligomers of propylene, styrenes etc. These processes can be batch, continuous or semi-continuous processes run in any type of reactor, e.g., kettle, flow reactor etc. In a particular embodiment, the aromatic amine alkylation uses a fixed bed reactor system, e.g., a plug flow, fixed bed reactor system, for at least a part of the process.

The products obtained using the regenerated catalysts are the same as those obtained using fresh catalysts and continue to be low in color and can comprise predominately a single compound or a mixture of alkylated aromatics. For example, in the alkylation of diphenylamine with nonenes, a mixture of mono-alkyl and di-alkyl diphenyl amine, plus a minor or negligible amount of trialkyl diphenyl amine, is often obtained.

DESCRIPTION OF THE INVENTION

Provided is a process for treating a spent or used catalyst, e.g., a clay catalyst, that has lost at least a portion of its catalytic activity due to use in alkylation reactions of aromatic compounds, comprising contacting said clay catalyst with a mixture, also called a regeneration mixture, comprising from 0.1 to 20 wt % of an acid, 1 to 45 wt % of water, and 35 to 98.9 wt % of an organic solvent, in an amount that is at least sufficient to fully wet the catalyst at a temperature of from 25 to 200° C., for from 0.5 to 36 hours, during which time the catalyst has regained at least a portion of its lost activity resulting in a regenerated clay catalyst, and then separating the regenerated clay catalyst from the regeneration mixture.

For example, the invention provides a catalyst regeneration process comprising contacting an alkylation catalyst, typically a clay catalyst, such as an acid clay catalyst, that has lost activity due to use in alkylation reactions, typically alkylation reactions of aromatic amines by olefins, with a regeneration mixture, comprising from 0.1 to 20 wt % of an acid, 1 to 45 wt % of water, and 35 to 98.9 wt % of an organic solvent at temperatures ranging from 25 to 200° C. for from 0.5 to 36 hours. In many embodiments the process comprises rinsing and/or soaking the used alkylation catalyst in the regeneration mixture. There is no limitation on the pressure under which the exposure of the catalyst to the regeneration process is carried out, but typically the process is run at ambient pressure or higher. Once the used catalyst has been regenerated, it is separated from the regeneration mixture and may optionally be post treated to remove water or other unwanted components.

The catalysts are typically clays, e.g., aluminosilicates, and may be naturally occurring, such as bauxite or mordenite clay, or a synthetic material, and may comprise alumina, silica, magnesia, zirconia or other compounds exhibiting similar properties. Many clays effective in the present process are commercially available and are well known in the art.

Commercial clay catalysts often contain some water that is generally removed prior to use in alkylation reactions to provide a lighter colored product and to improve performance. A variety of methods for reducing water content in clays are known, for example, vacuum stripping, heating the clay with a nitrogen sweep, azeotroping with organic liquids such as solvents or possible reactants such as olefins, and the like, and any such method may be used, if desired, to dry the regenerated catalyst after exposure to the acid/water/organic solvent mixture.

Clays most useful as catalysts for alkylating aromatic amines, and thus of high interest to the present invention, are typically "acid treated clays", "acid activated clays" or "acidic clays", the terms are used interchangeably herein, and can include those used for bleaching oils and waxes. For example, useful clays include sub-bentonite or bentonite clays, consisting predominantly of the clay mineral montmorillonite. For example, acid active bentonite clays useful as catalysts include F24X, F-24, F20X, F22B presently sold by BASF, formerly from ENGELHARD. Other commercially available clays include those sold as FILTROL 24, FILTROL 25 and FILTROL 62, FULCAT 14, FULCAT 22B, FULMONT 700C, FULMONT 237, KATALYSATOR, Attapulgus clay and Tonsil clay.

The used catalyst can be regenerated at any point of lost or retained activity, for example, the process of the invention can be used to restore the activity of a catalyst that has lost as little as a few percent of its original activity or one that is completely, or nearly completely, spent.

The regeneration process of the invention can be run as part of an overall alkylation process, wherein after the catalyst has lost at least a portion of its activity it is regenerated and then reintroduced into the process, or the regeneration process can be run on an otherwise obtained used catalyst. When integrated into a alkylation process, the regeneration process of the invention may be run in the same reactor as the alkylation reaction, but generally the catalyst is separated from the alkylation reaction mixture before regeneration.

Any method can be employed to separate the used clay from the bulk of the alkylation reaction/product mixture, typically, this is accomplished by the usual product isolation procedures, e.g., filtering, decanting, siphoning, distillation, etc. No additional treatment of the catalyst is necessary before exposure the regeneration mixture, however, one may choose to further wash, rinse, dry, or otherwise treat the catalyst prior to regeneration. For example, one may force air or an inert gas through the catalyst, remove materials under heat and or vacuum, rinse with an aqueous or organic solvent etc. One may choose to rinse the used catalyst with a solvent and then remove remnants of the solvent by vaporization of the solvent prior to catalyst regeneration, but in many embodiments this is unnecessary.

Contacting the catalyst with the regeneration mixture can be accomplished by any convenient method. In many embodiments elevated temperatures will be used in this step. In some embodiments, the desired amount of regeneration may be accomplished by passing the regeneration mixture through the catalyst, for example, the catalyst may be placed on a filter while the mixture of acid/water/organic solvent is run through the catalyst either at ambient or elevated temperature. In some embodiments this is done in-line, e.g., the catalyst may be positioned in a plug flow reactor while the regeneration mixture is passed through the reactor. In other embodiments, the catalyst is wetted or suspended in the acid/water/organic solvent regeneration mixture and held at the desired temperature for a period of time, with or without mixing, before the regeneration mixture is separated. In some embodiments, the catalyst is both rinsed with the regeneration mixture and then held in contact with the mixture.

For example, in some embodiments the catalyst and acid/water/organic solvent mixture is held in a container at the desired temperature, e.g., a reaction vessel, flask, tank etc., for the selected time after which the acid/water/organic solvent mixture is removed by, e.g., filtration, siphon, or other like method. The regenerated catalyst can then be used as is or further treated by rinsing, drying or other optional process as described above.

In one particular embodiment the used catalyst is contained within a plug flow reactor, which is often, but not necessarily, the same reactor in which the alkylation reaction that lead to the deactivation of the catalyst is being run. For example, the reaction product mixture is pushed through the reactor as usual, after which the reactor is typically flushed with an organic solvent, then the used catalyst is rinsed with the acid/water/organic solvent regeneration mixture and/or a volume of the acid/water/regeneration mixture is added to the reactor and held within the reactor at the desired temperature, e.g., the reflux or boiling point of the regeneration mixture, for a period of time, e.g., 0.5 to 36 hours, often from 1 to 24 hours or 2 to 16 hours, and then the regeneration mixture is drained from the reactor. The regenerated catalyst is then typically rinsed, e.g., with an organic solvent or other organic liquid, and optionally dried before the reaction is recommenced. In some embodiments, the regenerated catalyst is rinsed with the alkene used to alkylate the aromatic amine before the reaction is recommenced.

A wide variety of acids and organic solvents can be used in the acid/water/organic solvent regeneration mixture and the exact composition may vary depending on the catalyst being regenerated and the chemical reaction in which the catalyst had been used. The relative concentrations of acid, water and organic solvent may also depend somewhat on the specific acids and solvents used.

The acid component may be an organic acid, such as acetic acid, propanoic acid, etc., an inorganic acid, or a mixture thereof. In many embodiments the acid component comprises an inorganic acid, e.g., a sulfur containing acid such as sulfuric acid, a halogen acid such as hydrochloric acid, a phosphorus acid such as phosphoric acid, and the like.

The organic solvent may comprise an alcohol, ether, hydrocarbon, ketone, ester, amide etc., in many embodiments the organic solvent comprises an alcohol such as a $C_1$-$C_{12}$ alcohol, ether such as t-butyl methyl ether or t-amyl ethyl ether or a furanyl ether, saturated hydrocarbon such as a $C_6$-$C_{12}$ alkane, aromatic hydrocarbon such as benzene or alkylated benzene, or ketone such as a $C_1$-$C_{10}$ ketone. For example, the organic solvent often comprises methanol, ethanol, propanol, iso-propanol, butanol, iso-, sec- or tert-butanol, pentanol, hexanol, heptanol, octanol, ethylhexanol and the like; hexane, cyclohexane, petroleum ethers, toluene, xylene, mesitylene, etc.; or acetone, methyl ethyl ketone, and the like. Halogenated solvents may be used, e.g., methylene chloride, chloroform etc., but may not be optimal due to environmental concerns etc.

The amount of acid in the regeneration mixture can range from 0.1 to 20 wt %. Often the upper limit of acid will be 10 wt %, e.g., 5 wt %. The lower limit of acid in some embodiments is 0.5 wt %, e.g., 1 wt %. The amount of water can range from 1 to 45 wt %. In many embodiments the upper limit of water is 40 wt %, e.g., 30 wt % or 25 wt %. The lower limit of water in some embodiments is 2 wt %, e.g., 5 wt %. The remainder of the regeneration mixture is one or more organic solvents. Typically, at least 35 wt % of the mixture is organic solvent and in many embodiments more than 50 wt % is organic solvent.

In certain particular embodiments the regeneration mixture comprises from 0.1 to 15 wt %, or 0.5 to 10 wt % of the acid, 1 to 25 wt %, e.g., 1 to 20 wt % of the water, and 50 to 98.9 wt %, e.g., 70 to 98.5 wt % of the organic solvent.

It is possible to successfully regenerate the same sample of catalyst multiple times with excellent results. However, when regenerating a catalyst according to the invention, one should choose conditions, e.g., ratios of acid/water/organic solvent, temperature, contact time, organic solvent selection etc., as taught herein to minimize any deleterious impact that regeneration may have on the physical integrity of the catalyst. For example, clay catalysts are known to have a particular structure comprising active moieties on the surface, and if the conditions chosen for regeneration are overly harsh or otherwise inappropriate, the structural integrity or the surface activity may be harmed. Large scale physical destruction of the catalyst is also possible.

For example, treating some spent clays with water or steam can provide some positive regeneration effect on catalyst activity. However, it was discovered that water is destructive to the granulated form of many clay catalysts. For example, treatment of fresh clay catalysts with water often produces a fine silt leading to hazy products, plugged filters, and restricted or blocked flow of reactants through the catalyst bed of a flow reactor. The use of methanol instead of water provided mainly negligible regeneration but still lead to physical destruction of some of the catalysts. The degree of catalyst destruction varied depending on the catalyst. The structure of a used or spent clay catalyst is not necessarily the same as the fresh catalyst, and used catalysts may have absorbed or incorporated other components, or may have become coated with modified clay substrates or foreign materials. However, the risk of damage to a used clay catalysts during an overly aggressive regeneration process remains.

To obtain a preliminary evaluation of the suitability of solvents, fresh clay catalysts were exposed to series of solvents and then examined for possible physical degradation. In the following table, haze refers to a small of moderate amount of degradation leading to haze appearing in the solvent, none refers to an undetectable amount of physical decomposition, and total meant no granular form of the catalysts remained after exposure. F24X is reported to be an agglomerated version of the catalyst F20X, and it is not surprising perhaps that destruction of the agglomerated particle in aggressive solvents occurs to such a large extent.

| Solvent | Fulcat 22B | F24 | F24X |
|---|---|---|---|
| Water | Near total | Haze | Total |
| methanol | None | Haze | Total |
| ethanol | None | Haze | Total |
| isopropanol | None | Haze | Near total |
| 1-hexanol | None | Haze | Near total |
| acetonitrile | None | Haze | Total |
| acetone | None | Haze | Total |
| t-amyl-methyl-ether | None | None | Haze |
| chloroform | None | None | None |
| Toluene | None | None | None |

Exposing used catalysts to mixtures of organic solvents and water, such as methanol/water, demonstrated some positive regeneration effects, but at low water concentrations, e.g., 5% or less of water, the effect was negligible. The inclusion of a small amount of acid in the mixture greatly boosted the degree of catalyst regeneration.

As mentioned above, U.S. Pat. No. 4,824,601 discloses that reacting diphenylamine with alkenes in the presence of certain clay catalysts at certain molar ratios within specific temperature ranges for a certain amount of time will provide an alkylated product as a mixture of mono- and poly-alkylated materials containing less than 25% di-alkylated diphenylamine. When using a fixed bed flow reactor, the reaction time depends on the flow rate. While a faster flow rate can increase the efficiency of the process by generating more product in a given amount of time, the selectivity of the reaction may also depend, among other factors, on the flow rate. The actual flow rate will then typically reflect a balance between overall product yield and selectivity. One measure of catalyst activity is found in the change of product distribution, i.e., a change in the relative amounts of mono- and di-alkylation products. Successful periodic regeneration of the catalyst by the process of the present invention allows one to maintain consistent production rates of product within the desired specifications.

However, it can be readily appreciated that regeneration of the catalyst accompanied by excessive catalyst destruction or unwanted modification will force one to replace the catalyst after a minimal number of regenerations. Because an excess of catalyst is typically used at the beginning of a reaction, it is not always clear the amount of catalyst that may be destroyed during regeneration. In some experiments, a mixture of methanol, water and strong acid was very effective at regenerating catalyst activity, but the catalyst activity dropped off over repeated regeneration steps. Initial experiments wherein the methanol was replaced with isopropanol in the regeneration mixture provided less regained catalyst activity after the first regeneration procedure, but in general isopropanol appears to be less destructive to the catalyst. Of course, the actual results will vary depending on a variety of factors, and the details pertaining to the behavior and results of a particular protocol should be tested and adjusted where necessary.

One must keep in mind that a particular regeneration solvent may provide a high degree of regained catalyst activity, but this may coincide with an unwanted degree of catalyst loss, which may differ depending on, e.g., the catalyst employed.

Results will vary depending on the specific clay catalysts used, however, while water, acids, and certain solvents can be highly destructive to certain bentonite clays, excellent results have been obtained by selecting the appropriate components at the proper concentrations according to the teachings of the present invention. It is expected that it is well within the skill of one skilled in the art to optimize the regeneration mixture and process of the invention to suit the needs of a particular catalyst being used in a particular alkylation reaction through routine experimentation.

As mentioned above, various embodiments are to a process for alkylating an aromatic amine that incorporates the present catalyst regeneration process. One particular embodiment provides an improved process for alkylating an aromatic amine in a fixed bed flow reactor wherein the catalyst is periodically regenerated, typically without removing the catalyst from the fixed bed reactor.

For example, in one embodiment a process for alkylating an aromatic amine comprises:
A) passing a mixture comprising one or more olefins and an aromatic amine of formula through an acidic clay catalyst in a fixed bed reactor to yield the alkylation product;
B) discontinuing passage of the one or more olefins and aromatic amine through the acidic clay catalyst;
C) contacting the acidic clay catalyst with the acid/water/organic regeneration mixture e.g., rinsing and/or soaking the used acidic clay catalyst in the regeneration mixture, at temperatures ranging from 25 to 200° C. to regenerate catalyst activity as described above to form a regenerated clay catalyst, and typically,
D) resuming passage of the one or more olefins and aromatic amine through the regenerated clay catalyst,
wherein the acidic clay catalyst remains in the fixed bed reactor throughout steps A through D. Steps A) through D) may be repeated in a continuous cycle.

In addition to steps A) through D), the process will typically also comprise flushing the reactor and catalysts bed with an organic solvent and/or a gas such as nitrogen or air in order to prevent significant contact between the reaction feed and the regeneration mixture. For example, after passage of the one or more olefins and aromatic amine through the acidic clay is discontinued, the reactor and catalyst may be flushed with nitrogen and/or an organic solvent before contacting the clay catalyst with the regeneration mixture. Likewise, steps such as flushing with nitrogen and/or organic solvent will generally take place after the catalyst has been in contact with regeneration mixture and before resuming passage of the reactants through the catalyst bed to avoid contamination of the feed.

Generally in step A, the one or more olefins are selected from the group of $C_{3-20}$ olefins, and the aromatic amine has a formula:

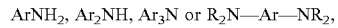

wherein each Ar of the aromatic amine starting material is independently selected from the group consisting of phenyl, phenyl substituted by $C_{1-18}$ alkyl, naphthyl, and naphthyl substituted by $C_{1-18}$ alkyl;

and each R is independently selected from the group consisting of H, $C_{1-18}$ alkyl, phenyl, phenyl substituted by $C_{1-18}$ alkyl, naphthyl, and naphthyl substituted by $C_{1-18}$ alkyl.

In many embodiments the aromatic amine has a formula:

$ArNH_2$, $Ar_2NH$, $Ar_3N$ or $R_2N$—Ar—$NR_2$, wherein each Ar is independently selected from the group consisting of phenyl, phenyl substituted by $C_{1-12}$ alkyl, naphthyl, and naphthyl substituted by $C_{1-12}$ alkyl; for example phenyl, phenyl substituted by $C_{1-12}$ alkyl or naphthyl; for example, phenyl, phenyl substituted by $C_{1-9}$ alkyl or naphthyl;

and each R is independently selected from the group consisting of H, $C_{1-18}$ alkyl, phenyl, phenyl substituted by $C_{1-18}$ alkyl, and naphthyl, e.g., H, $C_{1-12}$ alkyl, phenyl or phenyl substituted by $C_{1-12}$ alkyl; e.g., H, $C_{1-12}$ alkyl, phenyl.

Certain embodiments relate to the alkylation of an aromatic amine of formula $Ar_2NH$ or $R_2N$—Ar—$NR_2$, for example, $Ar_2NH$.

The reaction parameters for step A) are known in the art and reaction typically takes place at temperatures of from 50 to 250° C. and at ambient or elevated pressures.

Depending on the reaction and reactor setup, step B) may further comprise, after discontinuing passage of the one or more olefins and aromatic amine through the acidic clay catalyst, flushing the acidic clay catalyst with organic or aqueous solvent, mixtures of solvents, and/or a gas such as air or an inert gas.

Step C) may be carried out according the any of the variants discussed herein for contacting the clay catalyst with an acid/water/organic solvent mixture, and may further comprise flushing the regenerated acidic clay catalyst with organic or aqueous solvent, mixtures of solvents, and/or a gas such as air or an inert gas; drying the regenerated acidic clay catalyst using heat and/or reduced pressure; or other further steps to insure catalytic activity, etc.

Conveniently, the entire process can be run without removing the clay catalyst from the plug flow reactor. In running the process, the components of the olefin/aromatic amine feed can be changed or modified at any point and additional catalyst may be added if desired. The process is most efficiently run as a continuous or semi-continuous process.

In particular examples, the improved alkylation process of the invention is used to alkylate di-aromatic amines, such as diphenylamine, dinaphthylamine, N-phenyl-1-naphthylamine, N-phenyl-2-naphthylamine, p-methylamino-diphenylamine, p-isopropylamino-diphenylamine and the like.

The $C_{3-20}$ olefins used in the present method are well known and include propene, butene, pentene, hexene, octene, nonene, mixtures of nonenes, decene, undecene, dodecene, tetradecene, hexadecene octadecene and the like, including straight chain or branched isomers and isomers differing by the placement of the double bond, for example, 1-nonene, 2-nonene etc., and n-butene, iso-butene, isooctene, 2-ethylhexene and the like. Mixtures of olefins are often employed. In some select embodiments the olefins are derived from propene or isobutylene, e.g., certain embodiments the one or more olefins comprise one or more of isobutylene, di-isobutylene, tri-isobutylene, di-propylene, tri-propylene and the like. Often, the olefin will comprise mixtures of propylene and butylene oligomers, e.g., oligomer mixtures comprising propylene or butylene dimers, trimers and/or tetramers etc., which mixtures often include the monomeric species. In certain embodiments the one or more olefins comprise isobutylene, di-isobutylene, tri-isobutylene, di-propylene, tri-propylene or tetrapropylene.

The reactions are often run under pressures greater than atmospheric. In some cases this is due the pressure created by forcing the reactants through the catalyst at a specified flow rate.

In the case of very volatile olefins, e.g., propene, butene and iso-butene, or when the selected olefin has a boiling point below the reaction temperature, higher pressure is highly desired.

In many embodiments the one or more olefins is selected from the group of $C_{6-18}$ olefins, for example, $C_{8-18}$ olefins or $C_{8-12}$ olefins, such as diisobutylene and nonenes. In many cases, such as when nonene is obtained by trimerization of propylene, a mixture of nonenes will be present.

The mole ratio of the one or more olefins to the aromatic amine is generally from about 0.8 or about 1:1 to about 5:1, e.g., from about 1:1 to about 4:1 or from about 1:1 to about 3:1. While the process can be run using equimolar amounts of olefin and amine, it is generally run using a higher amount of olefin, for example, the mole ratio of the one or more olefins to the aromatic amine is often from about 1.1:1, 1.2 or 1.3 to about 5:1 or 4:1, e.g., from about 1.3:1 to about 4:1, from about 1:5 to about 4:1, or from about 2:1 to about 4:1. Unreacted amine, olefin or olefin byproducts, e.g., olefin oligomers or cracking products, can be removed from the product mixture using standard techniques, such as distillation.

In particular embodiments, the clay is F-24X, F-24 or F-22B which is pretreated to remove water, and often the pretreatment also removes dust. For example, in some instances the catalyst may be packed in a column and rinsed with a solvent to remove dust and draw moisture out after which the catalyst can be dried in an oven if desired. In some embodiments crude reaction product or alkenes used in the reaction can be passed through the column containing the catalyst. Other methods are known and may be used. Often, the bottom of the reactor tube is packed with fine material (glass wool, sand, fine alumina or F-20X clay) to prevent the passage of catalyst dust.

The reaction is typically run in a reactor heated at a temperature of from about 50 to about 250° C., for example from about 100 to about 200° C. and in some embodiments from about 140 to about 180° C. The reaction can be carried out at a single temperature or, sequentially, at different temperatures. In some cases, the reaction may cause enough of an exotherm which will require a means for dissipating excess heat. Adjusting the rate at which individual reactants are added may also impact the reaction temperature.

The starting materials may be preheated prior to introduction to the reactor. In some embodiments one or more of the reactants are solid at room temperature and the solid component or a mixture comprising the solid component is heated to a temperature to keep the component or the mixture liquid.

If desired, the reaction can be carried out in a neutral solvent such as an inert hydrocarbon solvent, but generally no solvent is necessary. In some embodiments, the use of an excess of olefin can act as a solvent. Inert gas, such as nitrogen, can be used to minimize oxidation of products during reaction, but mostly to allow operation at higher temperatures with the lower boiling oligomers.

The olefin and aromatic amine reactants can be introduced into the reactor separately through different individual feeds, separately but through the same line, or they may be mixed together before being introduced to the fixed bed reactor through the same feed. For example, the reactants may be mixed together in a vessel and the resulting mixture may be introduced to the reactor through a single feed. It is also possible to introduce a reaction mixture into the reactor and then introduce additional doses of one or more reactants at a later point, often using additional feeds.

Typically, the reactants are pumped into and through the reactor. The rate of flow through the catalyst can thus be controlled by adjusting the pump. A certain amount of increased pressure within the reactor will generally exist due to the back pressure created by the flow of reactants though the catalyst bed or other points in the reactor system, faster feed rates generating higher pressure. It is also possible to draw the reactants through the reactor by pumping the reaction mixture out after passage through the reactor and control the flow rate by adjusting, e.g., a post reactor pump, but any suitable means for controlling the flow rate may be used.

Typically the pressure under which the reaction occurs is, at least partially, a function of the olefin used, the reaction temperature, the flow rate, and/or the clay catalyst selected. The reaction pressure can range up to about 250 psi or higher, but is often below about 250 psi, and frequently 100 psi or less and in some embodiments the reaction can be run at roughly atmospheric pressure. In some particular reactions one may choose to run the reaction under reduced pressure.

One particular embodiment relates to the alkylation of diphenylamine, preferably in the 4 position or in the 4 and 4' positions, providing alkylated diphenylamines, which are known as effective antioxidants, for example, reaction of diphenyl amine with nonenes, 2,4,4-trimethylpentene and the like to produce commercially valuable alkylated diphenylamines, often as a mixture of mono- and di-alkylated compounds, many of which are liquids. Often, these antioxidants are prepared in a specified ratio of mono- to di- to tris-alkylation products. The catalyst regenerated according to the process of the invention will typically maintain a useful selectivity or producing these specified mixtures of products.

EXAMPLES

A stainless-steel tube (1 inch diameter, 13 inches in length) was charged with 73.0 grams of an acid active bentonite clay, F24X, or F22B available from BYK, presieved through a 20 mesh to standardize particle size, which catalyst was preheated to 160° C. and purged with nitrogen to remove water. Nonenes and diphenylamine were mixed in a 2.2:1 mass ratio, i.e., 3.0:1 mole ratio (nonenes:DPA) and heated to avoid precipitation of diphenylamine. The heated reactant mixture was pumped into the reactor. When the catalyst activity dropped to an unsuitable level the catalyst was regenerated and the reaction restarted.

To regenerate the catalyst, without removing the catalyst from the reactor, the reactant flow was stopped. The column was then purged with nitrogen for 2 hours at reaction temperature before cooling to 90° C., at which point about 50 ml of a 200 ml acid/water/organic solvent regeneration mixture was poured through the column at a high rate, after which the catalyst bed remained submerged in the regeneration mixture for 16 hours at 90° C. The column was then drained, rinsed quickly with another 50-100 ml of the regeneration mixture, purged with nitrogen for 15 min and rinsed with 50 mL isopropanol. The column temperature was then raised to reaction temperature and purged with nitrogen for 2 hours before restarting the reactant feed.

In the following tables, the time refers to the number of hours the reaction was run using the virgin catalyst, the catalyst after the first regeneration and the catalyst after the second regeneration, WHSV is the rate at which the reactants were passed through the reactor, the temperature is the reaction temperature, and gP/gC is the ratio of grams of product per gram of catalyst. The composition of the regeneration mixture is found in the Table heading in percent by weight.

1% Sulfuric Acid/9% Water/90% Methanol

| F24X | Time | WHSV (hr$^{-1}$) | Temp C. | gP/gC |
|---|---|---|---|---|
| Virgin | 45.1 | 0.42 | 170 | 13.3 |
| Regen 1 | 49.6 | 0.39 | 170 | 13.5 |
| Regen 2 | 36.7 | 0.39 | 170 | 10.0 |
| Sum/Ave | 131.4 | 0.40 | 170 | 36.8 |

1% Sulfuric Acid/9% Water/90% Isopropanol

| F24X | Time | WHSV | Temp C. | gP/gC |
|---|---|---|---|---|
| Virgin | 41.2 | 0.41 | 170 | 11.8 |
| Regen 1 | 38.0 | 0.37 | 170 | 9.8 |
| Regen 2 | 28.9 | 0.38 | 170 | 7.7 |
| Sum/Ave | 108.1 | 0.39 | 170 | 29.4 |

1% Phosphoric Acid/9% Water/90% Isopropanol

| F24X | Time | WHSV | Temp C. | gP/gC |
|---|---|---|---|---|
| Virgin | 45.5 | 0.36 | 165 | 11.5 |
| Regen 1 | 48.5 | 0.31 | 165 | 10.5 |
| Regen 2 | 28.9 | 0.38 | 165 | 6.3 |
| Sum/Ave | 122.9 | 0.33 | 165 | 28.3 |

1% Sulfuric Acid/9% Water/90% Isopropanol

| F22b | Time | WHSV | Temp C. | gP/gC |
|---|---|---|---|---|
| Virgin | 106 | 0.32 | 160 | 23.7 |
| Regen 1 | 57 | 0.32 | 160 | 12.8 |
| Regen 2 | 37 | 0.32 | 160 | 8.3 |
| Sum/Ave | 200 | 0.32 | 160 | 44.8 |

What is claimed:

1. A process for treating a clay catalyst that has lost at least a portion of its catalytic activity due to use in an alkylation reaction of an aromatic compound, said process comprising providing a clay catalyst that has lost at least a portion of its catalytic activity due to use in an alkylation reaction of an aromatic compound, contacting said clay catalyst with a regeneration mixture comprising from 0.1 to 20 wt % of an acid, 1 to 45 wt % of water, and 35 to 98.9 wt % of an organic solvent, in an amount that is at least sufficient to fully wet the catalyst, at a temperature of from 25 to 200° C., for from 0.5 to 36 hours, during which time the clay catalyst has regained at least a portion of its lost activity resulting in a regenerated clay catalyst, and then separating the regenerated clay catalyst from the regeneration mixture.

2. The process according to claim 1, wherein the regeneration mixture comprises from 0.5 to 10 wt % of the acid, 1 to 20 wt % of the water, and 70 to 98.5 wt % of the organic solvent.

3. The process according to claim 1, wherein the acid comprises an inorganic acid.

4. The process according to claim 1, wherein the acid comprises an organic acid.

5. The process according to claim 1, wherein the organic solvent comprises an alcohol, ketone, ether or hydrocarbon.

6. The process according to claim 1, wherein the organic solvent comprises methanol, ethanol, propanol, isopropanol, butanol, isobutanol, sec-butanol, tert-butanol, amyl alcohol, iso amyl alcohol, sec-amyl alcohol, tert-amyl alcohol, acetone, ethyl methyl ketone, toluene, xylene or mesitylene.

7. The process according to claim 2, wherein the organic solvent comprises an alcohol, ketone, ether or hydrocarbon.

8. The process according to claim 1, wherein the clay catalyst that has lost at least a portion of its catalytic activity due to use in an alkylation reaction of an aromatic compound is an acidic clay catalyst that has lost at least a portion of its catalytic activity due to use in a reaction for alkylating an aromatic amine.

9. The process according to claim 8, wherein the acidic clay catalyst is a bentonite clay.

10. The process according to claim 8, further comprising reintroducing the regenerated clay catalyst to a reaction for alkylating an aromatic amine.

11. The process according to claim 10 comprising:
A) passing a mixture comprising one or more olefins and an aromatic amine through an acidic clay catalyst in a fixed bed reactor to yield an alkylation product;
B) discontinuing passage of the one or more olefins and aromatic amine through the acidic clay catalyst;
C) contacting the acid clay catalyst with a regeneration mixture comprising from 0.1 to 20 wt % of an acid, 1 to 45 wt % of water, and 35 to 98.9 wt % of an organic solvent, in an amount that is at least sufficient to fully wet the catalyst, at a temperature of from 25 to 200° C., for from 0.5 to 36 hours, during which time the clay catalyst has regained at least a portion of its lost activity resulting in a regenerated clay catalyst, and then separating the regenerated clay catalyst from the regeneration mixture, and
D) resuming passage of the one or more olefins and aromatic amine through the regenerated clay catalyst.

12. The process according to claim 11 wherein B) further comprises, after discontinuing passage of the one or more olefins and aromatic amine through the acidic clay catalyst, flushing the acidic clay catalyst with organic or aqueous solvent, mixtures of solvents, and/or air or an inert gas.

13. The process according to claim 11 wherein C) further comprises flushing the regenerated acidic clay catalyst with organic or aqueous solvent, mixtures of solvents, and/or air or an inert gas, drying the regenerated clay catalyst using heat and/or reduced pressure.

14. The process according to claim 12 wherein C) further comprises flushing the regenerated acidic clay catalyst with organic or aqueous solvent, mixtures of solvents, and/or air or an inert gas, drying the regenerated clay catalyst using heat and/or reduced pressure.

15. The process according to claim 11 wherein the process is carried out without removing the clay catalyst from the reactor.

16. The process according to claim 11 wherein the aromatic amine is diphenylamine, dinaphthylamine or N-phenyl-N-naphthyl amine.

17. The process according to claim 11 wherein the one or more olefins comprise isobutylene, di-isobutylene, tri-isobutylene, di-propylene, tri-propylene or tetra-propylene.

* * * * *